United States Patent
Jin et al.

(10) Patent No.: US 12,154,267 B2
(45) Date of Patent: Nov. 26, 2024

(54) FULLY AUTOMATIC INLINE PROCESSING FOR PC-MRI IMAGESFULLY AUTOMATIC INLINE PROCESSING FOR PC-MRI IMAGES USING MACHINE LEARNING

(71) Applicant: Siemens Healthineers AG, Forchheim (DE)

(72) Inventors: Ning Jin, Solon, OH (US); Teodora Chitiboi, Hamburg (DE)

(73) Assignee: Siemens Healthineers AG, Forchheim (DE)

( * ) Notice: Subject to any disclaimer, the term of this patent is extended or adjusted under 35 U.S.C. 154(b) by 396 days.

(21) Appl. No.: 17/249,198

(22) Filed: Feb. 23, 2021

(65) Prior Publication Data
US 2022/0270240 A1    Aug. 25, 2022

(51) Int. Cl.
*G06T 7/00*    (2017.01)
*G06N 3/08*    (2023.01)
(Continued)

(52) U.S. Cl.
CPC .............. *G06T 7/0012* (2013.01); *G06N 3/08* (2013.01); *G06T 5/70* (2024.01); *G06T 7/11* (2017.01);
(Continued)

(58) Field of Classification Search
CPC ......... G06T 7/0012; G06T 7/11; G06T 5/002; G06T 2207/10088; G06T 2207/20081;
(Continued)

(56) References Cited

U.S. PATENT DOCUMENTS

2012/0059269 A1 * 3/2012 Zhang .................... G16H 15/00
                                                       600/504
2016/0284089 A1 * 9/2016 Gulaka .................... G06T 7/33
(Continued)

FOREIGN PATENT DOCUMENTS

WO    WO-2022171416 A1 * 8/2022 ........... G06T 7/0002

OTHER PUBLICATIONS

Deanfield et al., "Management of Grown Up Congenital Heart Disease," 2003, European Heart Journal, vol. 24, Issue 11, pp. 1035-1084.
(Continued)

*Primary Examiner* — Vu Le
*Assistant Examiner* — Winta Gebreslassie

(57) ABSTRACT

Systems and methods for automatic processing of input medical images are provided. A set of input medical images acquired at a plurality of locations on a patient is received. For each respective location of the plurality of locations, an image quality score is determined for each input medical image of the set of input medical images acquired at the respective location and one of the input medical images acquired at the respective location is selected based on the image quality scores. The selected input medical images are processed to correct for errors. One or more regions of interest are segmented from the processed selected input medical images. One or more hemodynamic measures are calculated from the processed selected input medical images based on the segmented one or more regions of interest. The calculated one or more hemodynamic measures are output.

20 Claims, 6 Drawing Sheets

(51) Int. Cl.
*G06T 5/70* (2024.01)
*G06T 7/11* (2017.01)
*G16H 30/40* (2018.01)

(52) U.S. Cl.
CPC ... *G16H 30/40* (2018.01); *G06T 2207/10088* (2013.01); *G06T 2207/20081* (2013.01); *G06T 2207/30104* (2013.01); *G06T 2207/30168* (2013.01)

(58) Field of Classification Search
CPC ........... G06T 2207/30104; G06T 2207/30168; G16H 30/40; G06N 3/08
See application file for complete search history.

(56) References Cited

U.S. PATENT DOCUMENTS

2019/0122401 A1* 4/2019 Senzig .................. G06T 11/008
2019/0333210 A1* 10/2019 Mihalef ................ G06T 7/0012
2020/0077968 A1* 3/2020 Benishti ................. A61B 6/504
2023/0071400 A1* 3/2023 Abdolell ................ G16H 30/20

OTHER PUBLICATIONS

Silverman et al., "Phase-contrast cine MR angiography detection of thoracic aortic dissection," 2000, The International Journal of Cardiac Imaging, vol. 16, pp. 461-470.

Varaprasathan et al., "Quantification of Flow Dynamics in Congenital Heart Disease: Applications of Velocity-encoded Cine MR Imaging," 2002, RadioGraphics, vol. 22, No. 4, pp. 895-905.

Paulus et al., "How to diagnose diastolic heart failure: a consensus statement on the diagnosis of heart failure with normal left ventricular ejection fraction by the Heart Failure and Echocardiography Associations of the European Society of Cardiology," 2007, European Heart Journal, vol. 28, Issue 20, pp. 2539-2550.

* cited by examiner

100

```
┌─────────────────────────────────────────────────────────────────┐
│ Receive a set of input medical images acquired at a plurality   │
│ of locations on a patient                                       │
│ 102                                                             │
└─────────────────────────────────────────────────────────────────┘
                               ↓
┌─────────────────────────────────────────────────────────────────┐
│ Identify one or more anatomical landmarks depicted in the set   │
│ of input medical images                                         │
│ 104                                                             │
└─────────────────────────────────────────────────────────────────┘
                               ↓
┌─────────────────────────────────────────────────────────────────┐
│ For each respective location of the plurality of locations,     │
│ determine an image quality score for each input medical image   │
│ of the set of input medical images acquired at the respective   │
│ location and select one of the input medical images acquired    │
│ at the respective location based on the image quality scores    │
│ 106                                                             │
└─────────────────────────────────────────────────────────────────┘
                               ↓
┌─────────────────────────────────────────────────────────────────┐
│ Process the selected input medical images to correct for errors │
│ 108                                                             │
└─────────────────────────────────────────────────────────────────┘
                               ↓
┌─────────────────────────────────────────────────────────────────┐
│ Segment one or more regions of interest from the processed      │
│ selected input medical images                                   │
│ 110                                                             │
└─────────────────────────────────────────────────────────────────┘
                               ↓
┌─────────────────────────────────────────────────────────────────┐
│ Calculate one or more hemodynamic measures from the processed   │
│ selected input medical images based on the segmented one or     │
│ more regions of interest                                        │
│ 112                                                             │
└─────────────────────────────────────────────────────────────────┘
                               ↓
┌─────────────────────────────────────────────────────────────────┐
│ Output the calculated one or more hemodynamic measures          │
│ 114                                                             │
└─────────────────────────────────────────────────────────────────┘
```

Figure 1

FULLY AUTOMATIC INLINE PROCESSING FOR PC-MRI IMAGESFULLY AUTOMATIC INLINE PROCESSING FOR PC-MRI IMAGES USING MACHINE LEARNING

TECHNICAL FIELD

The present invention relates generally to processing for phase contrast magnetic resonance imaging (PC-MRI) images, and in particular to fully automatic inline processing for PC-MRI images using machine learning.

BACKGROUND

Phase contrast magnetic resonance imaging (PC-MRI) is a type of magnetic resonance imaging commonly used for visualizing and quantifying hemodynamics of a patient. PC-MRI has a variety of established applications for assessing cardiovascular function, such as, e.g., evaluation of vascular flow, aortic coarctation, aortic dissection, pulmonary blood flow, intracardiac shunts, diastolic function, valvular disease, etc. In the current clinical practice, PC-MRI images are manually post-processed offline by an operator to derive velocity and flow information. However, the manual post-processing of PC-MRI images is a time consuming and complicated process and may introduce subjectivity in the measurements.

BRIEF SUMMARY OF THE INVENTION

In accordance with one or more embodiments, systems and methods for automatic processing of input medical images are provided. A set of input medical images acquired at a plurality of locations on a patient is received. For each respective location of the plurality of locations, an image quality score is determined for each input medical image of the set of input medical images acquired at the respective location and one of the input medical images acquired at the respective location is selected based on the image quality scores. The selected input medical images are processed to correct for errors. One or more regions of interest are segmented from the processed selected input medical images. One or more hemodynamic measures are calculated from the processed selected input medical images based on the segmented one or more regions of interest. The calculated one or more hemodynamic measures are output.

In one embodiment, the selected input medical images are processed to correct for background phase errors. In another embodiment, the selected input medical images are processed to correct for phase aliasing artifacts.

In one embodiment, one or more anatomical landmarks depicted in the set of input medical images are identified. The one or more regions of interest may be segmented from the processed selected input medical images based on the identified one or more anatomical landmarks. The one or more hemodynamic measures may be calculated from the processed selected input medical images based on the identified one or more anatomical landmarks.

In one embodiment, the determining, the processing, and the segmenting are performed using a respective machine learning based model. In another embodiment, the determining, the processing, and the segmenting are performed using a single machine learning based model trained with multi-task learning.

In one embodiment, the hemodynamic measures comprise one or more of stroke volume, peak velocity inverse flow volume, and regurgitant fraction. The set of input medical images may comprise PC-MRI (phase contrast magnetic resonance imaging) images.

These and other advantages of the invention will be apparent to those of ordinary skill in the art by reference to the following detailed description and the accompanying drawings.

BRIEF DESCRIPTION OF THE DRAWINGS

FIG. 1 shows a method for automatic processing of medical images, in accordance with one or more embodiments;

DETAILED DESCRIPTION

Figure 2:
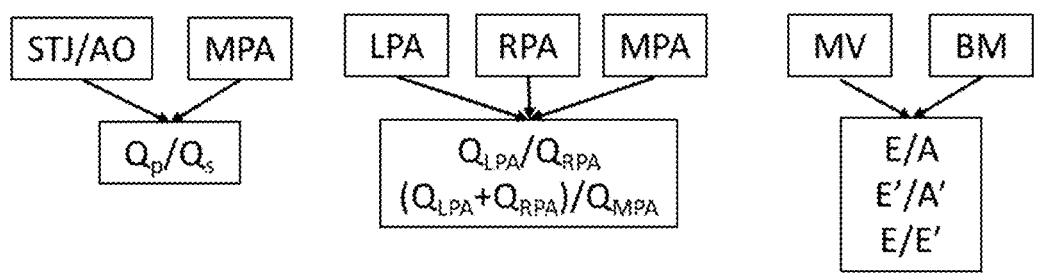
FIG. 2 shows various hemodynamic measures that may be calculated from a processed selected input medical image based on anatomical landmarks identified in the processed selected input medical image, in accordance with one or more embodiments.

The present invention generally relates to methods and systems for fully automatic inline processing for PC-MRI (phase contrast magnetic resonance imaging) images using machine learning. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein provide for fully automatic inline processing for PC-MRI images. One or more machine learning based models are applied to automatically perform, for example, image sorting, image quality scoring, segmentation, and assessment for the automatic processing of PC-MRI images. Advantageously, embodiments described herein may be implemented within an MRI scanner for automatic processing of PC-MRI images upon acquisition, while avoiding drawbacks associated with manual post-processing of PC-MRI images.

FIG. 1 shows a method 100 for automatic processing of medical images, in accordance with one or more embodiments. The steps of method 100 may be performed by one or more suitable computing devices, such as, e.g., computer 602 of FIG. 6.

At step 102, a set of input medical images acquired at a plurality of locations on a patient is received. The plurality of locations may include any suitable location on the patient. In one example, the plurality of locations are different locations of the heart of the patient.

In one embodiment, the set of input medical images comprises PC-MRI images. However, the set of input medical images may comprise any other suitable modality, such as, e.g., MRI (magnetic resonance imaging), ultrasound, x-ray, or any other medical imaging modality or combinations of medical imaging modalities. The set of input medical images may comprise 2D (two dimensional) images and/or 3D (three dimensional) volumes, and may comprise a single input medical image or a plurality of input medical images. In one embodiment, the set of input medical images comprises 2.5D (2D plus time) images. The set of input medical images may be received directly from an image acquisition device, such as, e.g., a MRI scanner, as the medical images are acquired, or can be received by loading previously acquired medical images from a storage or memory of a computer system or receiving medical images that have been transmitted from a remote computer system.

At step 104, optionally, one or more anatomical landmarks depicted in the set of input medical images are identified. The one or more anatomical landmarks may be any suitable anatomical landmarks of interest, such as, e.g., organs, bones, lesions, etc. In one example, the one or more anatomical landmarks may be anatomical landmarks associated with a heart of the patient, such as, e.g., the AO (aorta), the STJ (sinotubular junction), the AA (ascending aorta), the DA (descending aorta), the AV (aortic valve), the MPA (main pulmonary artery), the LPA (left pulmonary artery), the RPA (the right pulmonary artery), the MV (mitral valve), the TV (tricuspid valve), the BM (basal myocardial level), etc.

In one embodiment, the one or more anatomical landmarks may be identified using a machine learning based model. The machine learning based model may be a CNN or any other suitable machine learning based model. The machine learning based model may be trained during a prior offline or training stage based on training images manually annotated to identify anatomical landmarks therein. Once trained, the trained machine learning based model may be applied during an online or testing stage (e.g., step 104 of FIG. 1). The trained machine learning based model receives as input one or more input medical images and outputs one or more corresponding anatomical landmark for each of the one or more input medical images.

At step 106, for each respective location of the plurality of locations, an image quality score is determined for each input medical image of the set of input medical images acquired at the respective location and one of the input medical images acquired at the respective location is selected based on the image quality scores.

In one embodiment, the set of input medical images is first sorted based on the location on the patient at which each input medical image was acquired. If a plurality of input medical images is determined to have been acquired at the respective location based on the sorted set of input medical images, the image quality score is determined for each of the plurality of input medical images. The image quality score may be determined based on artifacts in the images. Such artifacts may include, e.g., blurring and streaking artifacts from respiratory motion in magnitude images, arrhythmia, flow pulsation, phase aliasing artifacts in phase images, etc. The image quality score may be determined based on any other suitable image quality attributes. One input medical image is selected from the plurality of input medical images acquired at the respective location based on the image quality scores. For example, an input medical image with a highest image quality score may be selected from the plurality of input medical images. If a single input medical image of the set of input medical images is determined to have been acquired at the respective location based on the sorted set of input medical images, that single input medical image may be selected without determining an image quality score for the single input medical image.

In one embodiment, the image quality score may be determined for each input medical image of the set of input medical images acquired at the respective location using a machine learning based model. The machine learning based model may be a CNN (convolutional neural network) or any other suitable machine learning based model. The machine learning based model may be trained during a prior offline or training stage based on training images (e.g., PC-MRI images) manually annotated with an image quality score by experienced users (e.g., radiologists). Once trained, the trained machine learning based model may be applied during an online or testing stage (e.g., step 106 of FIG. 1). The trained machine learning based model receives as input one or more input medical images and outputs a corresponding image quality score for each of the one or more input medical images.

At step 108, the selected input medical images are processed to correct for errors.

In one embodiment, where the selected input medical images are PC-MRI images, the PC-MRI images may be processed to correct for background phase errors. Background phase errors may be a result of eddy currents generated by the rapid switching of magnetic field gradients during MP-MRI image acquisition. If left uncorrected, smaller background phase errors may accumulate into larger errors when calculating flow and other hemodynamic measures. In one embodiment, the selected input medical images are processed to correct for background phase errors using a machine learning based model. The machine learning based model may be a CNN or any other suitable machine learning based model. The machine learning based model may be trained during a prior offline or training stage to automatically select stationary tissue while excluding regions affected by background phase error. The machine learning based model may be trained based on training images manually annotated to identify regions with background phase error Once trained, the trained machine learning based model may be applied during an online or testing stage (e.g., step 108 of FIG. 1). The trained machine learning based model receives as input the selected input medical images and outputs corresponding output images of the selected input medical images without regions affected by background phase error.

In one embodiment, the selected input medical images may be processed to correct for phase aliasing artifacts. During acquisition of PC-MRI images, a VENC (peak velocity encoding) value is selected by a user preferably at a value slightly higher than the maximum expected velocity. However, if the VENC value is selected to be lower than the true peak velocity, there is VENC aliasing in the phase images. As a result, pixels that should be bright with peak velocity in the positive direction appear dark, and vice versa. To correct for such phase aliasing artifacts, an anti-aliasing algorithm may be applied to the selected input medical images. The anti-aliasing algorithm may be any suitable anti-aliasing algorithm (e.g., known anti-aliasing algorithms).

At step 110, one or more regions of interest are segmented from the processed selected input medical images. The one or more regions of interest may be any regions of interest in the selected input medical images. In one embodiment, the regions of interest may comprise the one or more anatomical landmarks (identified at step 104) and the segmentation may be performed based on the identified one or more anatomical landmarks.

In one embodiment, the one or more regions of interest may be segmented from the processed selected input medical images using a machine learning based model. The machine learning based model may be a 2D/3D Unet or any other suitable machine learning based model. The machine learning based model may be trained during a prior offline or training stage based on training images depicting various regions of interest (e.g., various anatomical landmarks). In one example, the training images may be magnitude PC-MRI images or synthetic three channel images, each channel corresponding to magnitude, phase, and phase standard deviation over time. The training images may be manually annotated to identify the location of the regions of interest. Once trained, the trained machine learning based model may be applied during an online or testing stage (e.g., step 110 of FIG. 1). The trained machine learning based model receives as input the processed selected input medical images and possibly anatomical landmarks identified in the processed selected input medical images and outputs a corresponding segmentation map for each of the processed selected input medical images. In one embodiment, where the machine learning based model is a 3D Unet, the third dimension of the synthetic three channel images may be a temporal dimension in the image series. For example, the third dimension may be an entire temporal series or a subset of frames. A recurrent neural network may be used to integrate spatial information along the temporal dimension.

At step 112, one or more hemodynamic measures are calculated from the processed selected input medical images based on the segmented one or more regions of interest. The one or more hemodynamic measures may be calculated according to know equations based on data extracted from the processed selected input medical images. In one example, the one or more hemodynamic measures may include stroke volume, peak velocity inverse flow volume, regurgitant fraction, or any other blood flow parameters. The one or more hemodynamic measures may include additional hemodynamic measures based on the anatomical landmarks identified in the processed selected input medical images, as shown in FIG. 2.

FIG. 2 shows various hemodynamic measures that may be calculated from a processed selected input medical image based on anatomical landmarks identified in the processed selected input medical image, in accordance with one or more embodiments. As shown in FIG. 2, where the processed selected input medical image depicts the SJT/AO or the MPA, the hemodynamic measures may include the pulmonary to systolic flow ratio calculated as $Q_p/Q_s$, where $Q_p$ is the pulmonary flow and $Q_s$ is the systolic flow. Where the processed selected input medical image depicts the LPA, the RPA, or the MPA, the hemodynamic measures may include the LPA to RPA flow ratio calculated as $Q_{LPA}/Q_{RPA}$ or the LPA and RPA to MPA ratio calculated as $(Q_{LPA}+Q_{RPA})/Q_{MPA}$, where $Q_{LPA}$ is the LPA flow, $Q_{RPA}$ is the RPA flow, and $Q_{MPA}$ is the MPA flow. Where the processed selected input medical image depicts the MV or the BM, the hemodynamic measures may include the E/A ratio, the E'/A' ratio, or the E/E' ratio, where E is early left ventricular filling velocities, A is late or atrial left ventricular filling velocities, E' is longitudinal early myocardial filling velocities, and A' is late myocardial filling velocities.

In one embodiment, the calculated hemodynamic measures may be evaluated over time. For example, mean velocity, peak velocity, flow, area of region of interest, etc. may be evaluated over time. A graph or a curve may be generated showing the hemodynamic measures over time.

At step 114 of FIG. 1, the calculated one or more hemodynamic measures are output. For example, the calculated one or more hemodynamic measures can be output by displaying the calculated one or more hemodynamic measures on a display device of a computer system, storing the calculated one or more hemodynamic measures on a memory or storage of a computer system, or by transmitting the calculated one or more hemodynamic measures to a remote computer system.

As described above with respect to FIG. 1, one or more machine learning based models may be applied to perform various steps of method 100. The one or more machine learning based models applied in method 100 may be individual machine learning based models, separately trained to perform a respective medical imaging analysis task. However, in one embodiment, one or more (e.g., all) of the machine learning based models applied in method 100 may be combined into a single machine learning based model trained with multi-task learning to perform a plurality of medical imaging analysis tasks.

Figure 3:
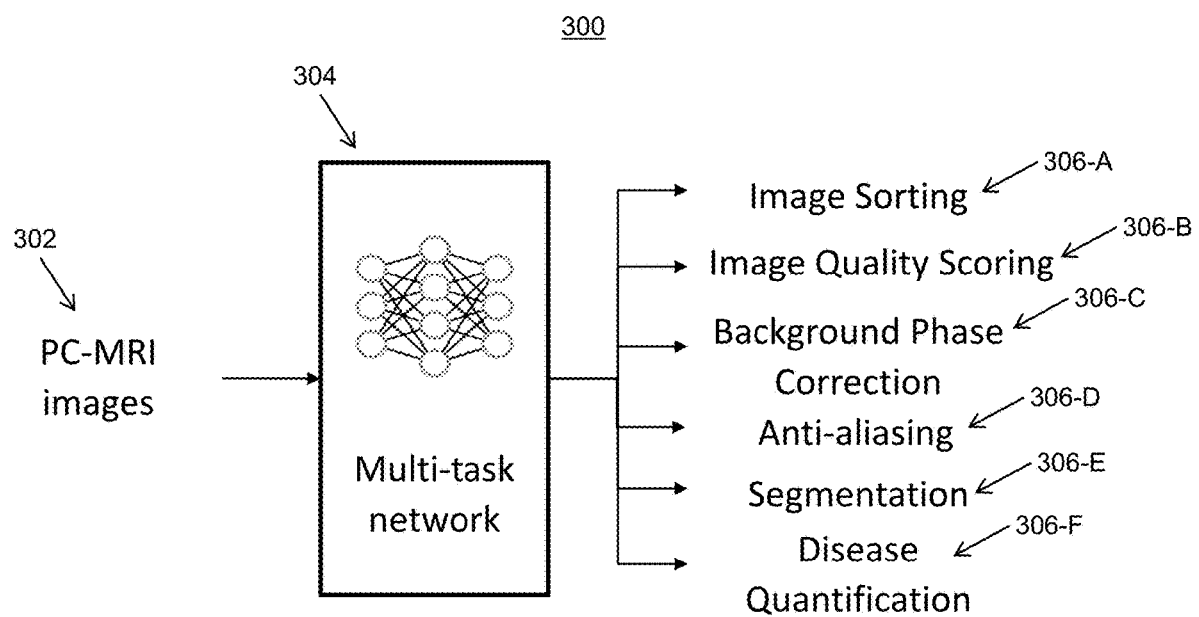
FIG. 3 shows a framework of a machine learning based model trained with multi-task learning to perform a plurality of medical imaging analysis tasks for calculating one or more hemodynamic measures, in accordance with one or more embodiments.

FIG. 3 shows a framework 300 of a machine learning based model trained with multi-task learning to perform a plurality of medical imaging analysis tasks for calculating one or more hemodynamic measures, in accordance with one or more embodiments. Framework 300 comprises a machine learning based multi-task network 304. Multi-task network 304 may represent one or more (e.g., all) of the machine learning based models applied in method 100. Multi-task network 304 comprises an encoder (not shown) and a plurality of decoders (not shown). The encoder receives as input PC-MRI images 302 and encodes PC-MRI images 302 into latent features. The plurality of decoders decode the latent features to perform a respective medical imaging analysis task. As shown in framework 300, the plurality of decoders decode the latent features to respectively perform image sorting 306-A, image quality scoring 306-B, background phase correction 306-C, anti-aliasing 306-D, segmentation 306-E, and disease quantification 306-F. By simultaneously training multi-task network 304 to perform the plurality of medical imaging analysis tasks, multi-task network 304 learns a more complete representation of the image context by using all of the available training information together (e.g., the location of a blood vessel, the stationary tissue, the areas with artifacts that should be avoided, etc.).

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 4:
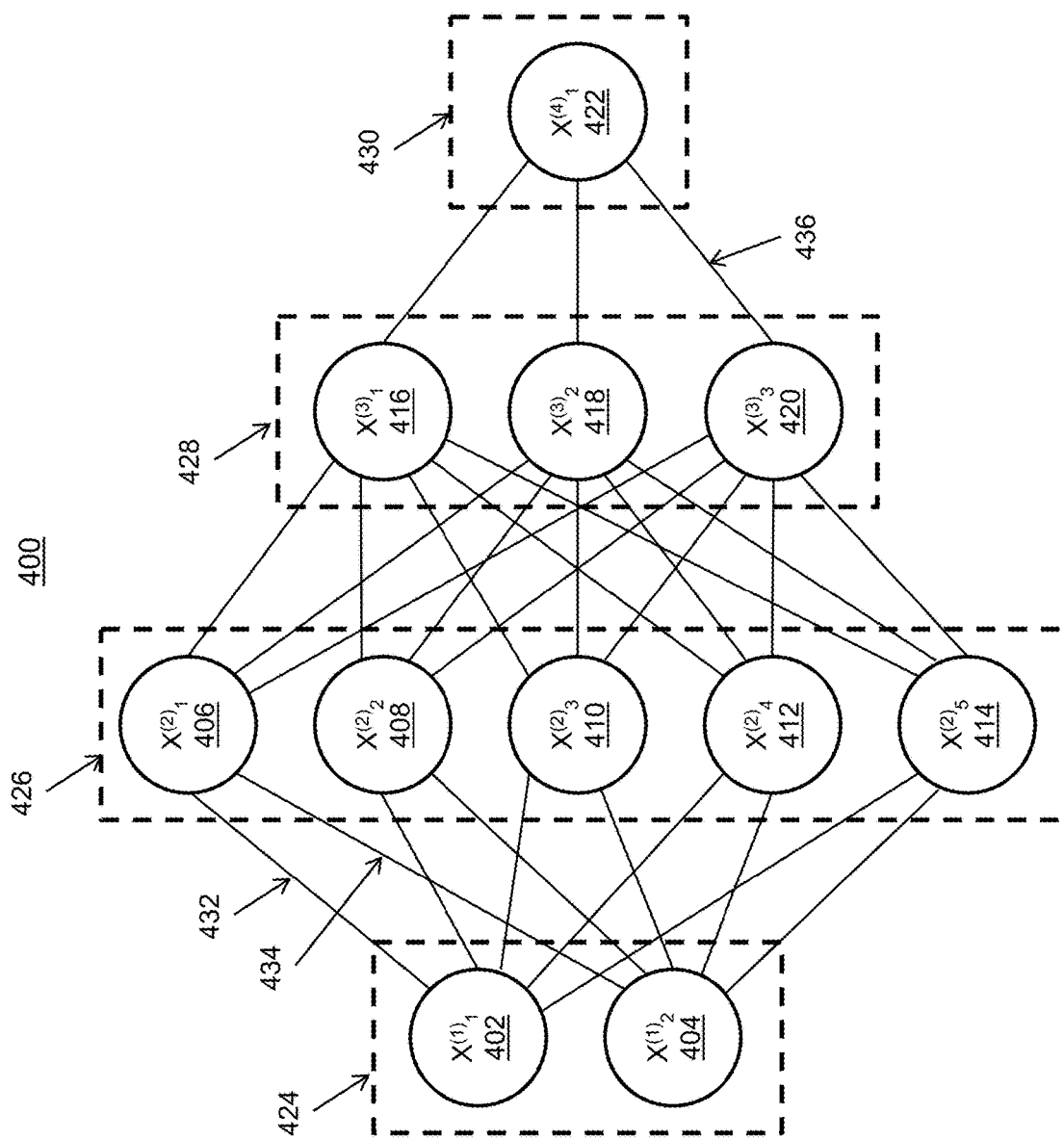
FIG. 4 shows an exemplary artificial neural network that may be used to implement one or more embodiments.

FIG. 4 shows an embodiment of an artificial neural network 400, in accordance with one or more embodiments. Alternative terms for "artificial neural network" are "neural network", "artificial neural net" or "neural net". Machine learning networks described herein, such as, e.g., the one or more machine learning based models utilized in method 100 of FIG. 1, may be implemented using artificial neural network 400.

The artificial neural network 400 comprises nodes 402-422 and edges 432, 434, . . . , 436, wherein each edge 432, 434, . . . , 436 is a directed connection from a first node 402-422 to a second node 402-422. In general, the first node 402-422 and the second node 402-422 are different nodes 402-422, it is also possible that the first node 402-422 and the second node 402-422 are identical. For example, in FIG. 4, the edge 432 is a directed connection from the node 402 to the node 406, and the edge 434 is a directed connection from the node 404 to the node 406. An edge 432, 434, . . . , 436 from a first node 402-422 to a second node 402-422 is also denoted as "ingoing edge" for the second node 402-422 and as "outgoing edge" for the first node 402-422.

In this embodiment, the nodes 402-422 of the artificial neural network 400 can be arranged in layers 424-430, wherein the layers can comprise an intrinsic order introduced by the edges 432, 434, . . . , 436 between the nodes 402-422. In particular, edges 432, 434, . . . , 436 can exist only between neighboring layers of nodes. In the embodiment shown in FIG. 4, there is an input layer 424 comprising only nodes 402 and 404 without an incoming edge, an output layer 430 comprising only node 422 without outgoing edges, and hidden layers 426, 428 in-between the input layer 424 and the output layer 430. In general, the number of hidden layers 426, 428 can be chosen arbitrarily. The number of nodes 402 and 404 within the input layer 424 usually relates to the number of input values of the neural network 400, and the number of nodes 422 within the output layer 430 usually relates to the number of output values of the neural network 400.

In particular, a (real) number can be assigned as a value to every node 402-422 of the neural network 400. Here, $x^{(n)}_i$ denotes the value of the i-th node 402-422 of the n-th layer 424-430. The values of the nodes 402-422 of the input layer 424 are equivalent to the input values of the neural network 400, the value of the node 422 of the output layer 430 is equivalent to the output value of the neural network 400. Furthermore, each edge 432, 434, . . . , 436 can comprise a weight being a real number, in particular, the weight is a real number within the interval [−1, 1] or within the interval [0, 1]. Here, $w^{(m,n)}_{i,j}$ denotes the weight of the edge between the i-th node 402-422 of the m-th layer 424-430 and the j-th node 402-422 of the n-th layer 424-430. Furthermore, the abbreviation $w^{(n)}_{i,j}$ is defined for the weight $w^{(n,n+1)}_{i,j}$.

In particular, to calculate the output values of the neural network 400, the input values are propagated through the neural network. In particular, the values of the nodes 402-422 of the (n+1)-th layer 424-430 can be calculated based on the values of the nodes 402-422 of the n-th layer 424-430 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 424 are given by the input of the neural network 400, wherein values of the first hidden layer 426 can be calculated based on the values of the input layer 424 of the neural network, wherein values of the second hidden layer 428 can be calculated based in the values of the first hidden layer 426, etc.

In order to set the values $w^{(m,n)}_{i,j}$ for the edges, the neural network 400 has to be trained using training data. In particular, training data comprises training input data and training output data (denoted as $t_i$). For a training step, the neural network 400 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 400 (backpropagation algorithm). In particular, the weights are changed according to $$w'^{(n)}_{i,j} = w^{(n)}_{i,j} - \gamma \cdot \delta^{(n)}_j \cdot x_i^{(n)}$$

wherein $\gamma$ is a learning rate, and the numbers $\delta^{(n)}_j$ can be recursively calculated as $$\delta^{(n)}_j = (\Sigma_k \delta_k^{(n+1)} \cdot w_{j,k}^{(n+1)}) \cdot f'(\Sigma_i x_i^{(n)} \cdot w_{i,j}^{(n)})$$

based on $\delta^{(n+1)}_j$, if the (n+1)-th layer is not the output layer, and $$\delta^{(n)}_j = (x_k^{(n+1)} - t_j^{(n+1)}) \cdot f'(\Sigma_i x_i^{(n)} \cdot w_{i,j}^{(n)})$$

if the (n+1)-th layer is the output layer 430, wherein f' is the first derivative of the activation function, and $y^{(n+1)}_j$ is the comparison training value for the j-th node of the output layer 430.

Figure 5:
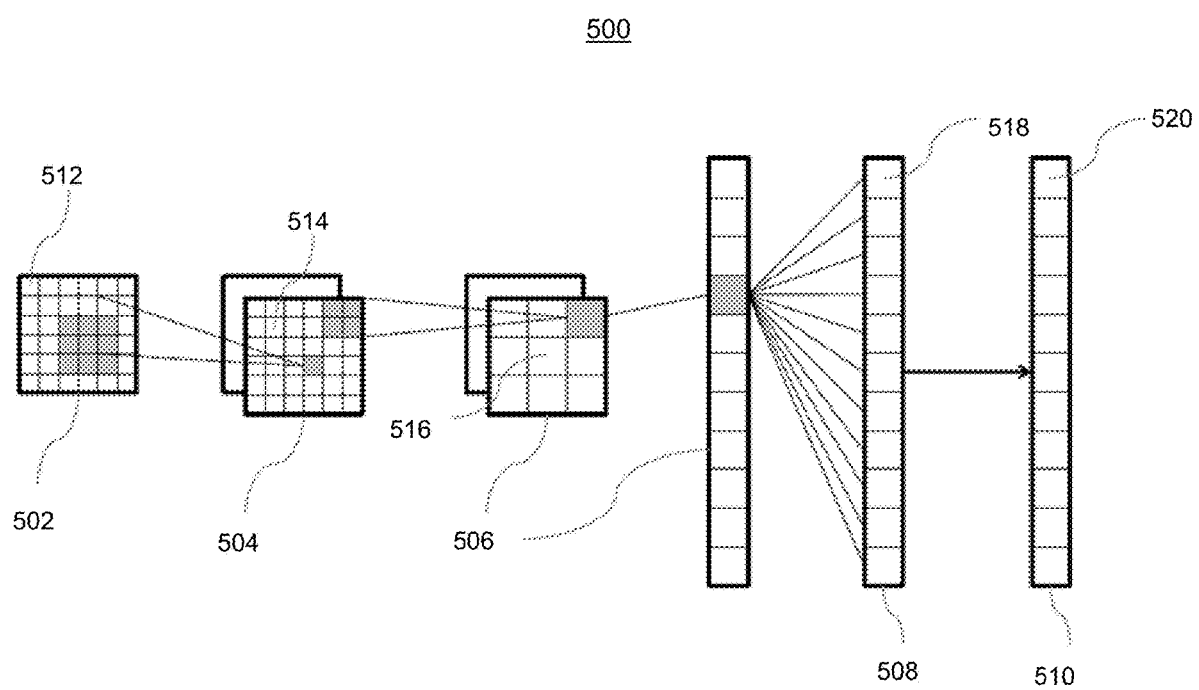
FIG. 5 shows a convolutional neural network that may be used to implement one or more embodiments.

FIG. 5 shows a convolutional neural network 500, in accordance with one or more embodiments. Machine learning networks described herein, such as, e.g., the one or more machine learning based models utilized in method 100 of FIG. 1, may be implemented using convolutional neural network 500.

In the embodiment shown in FIG. 5, the convolutional neural network comprises 500 an input layer 502, a convolutional layer 504, a pooling layer 506, a fully connected layer 508, and an output layer 510. Alternatively, the convolutional neural network 500 can comprise several convolutional layers 504, several pooling layers 506, and several fully connected layers 508, as well as other types of layers. The order of the layers can be chosen arbitrarily, usually fully connected layers 508 are used as the last layers before the output layer 510.

In particular, within a convolutional neural network 500, the nodes 512-520 of one layer 502-510 can be considered to be arranged as a d-dimensional matrix or as a d-dimensional image. In particular, in the two-dimensional case the value of the node 512-520 indexed with i and j in the n-th layer 502-510 can be denoted as $x^{(n)}_{[i,j]}$. However, the arrangement of the nodes 512-520 of one layer 502-510 does not have an effect on the calculations executed within the convolutional neural network 500 as such, since these are given solely by the structure and the weights of the edges.

In particular, a convolutional layer 504 is characterized by the structure and the weights of the incoming edges forming a convolution operation based on a certain number of kernels. In particular, the structure and the weights of the incoming edges are chosen such that the values $x^{(n)}_k$ of the nodes 514 of the convolutional layer 504 are calculated as a convolution $x^{(n)}_k = K_k * x^{(n-1)}$ based on the values $x^{(n-1)}$ of the nodes 512 of the preceding layer 502, where the convolution * is defined in the two-dimensional case as $$x_k^{(n)}[i,j] = (K_k * x^{(n-1)})[i,j] = \Sigma_i \Sigma_j K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 512-518 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 512-520 in the respective layer 502-510. In particular, for a convolutional layer 504, the number of nodes 514 in the convolutional layer is equivalent to the number of nodes 512 in the preceding layer 502 multiplied with the number of kernels.

If the nodes 512 of the preceding layer 502 are arranged as a d-dimensional matrix, using a plurality of kernels can be interpreted as adding a further dimension (denoted as "depth" dimension), so that the nodes 514 of the convolutional layer 504 are arranged as a (d+1)-dimensional matrix. If the nodes 512 of the preceding layer 502 are already arranged as a (d+1)-dimensional matrix comprising a depth dimension, using a plurality of kernels can be interpreted as expanding along the depth dimension, so that the nodes 514 of the convolutional layer 504 are arranged also as a (d+1)-dimensional matrix, wherein the size of the (d+1)-dimensional matrix with respect to the depth dimension is by a factor of the number of kernels larger than in the preceding layer 502.

The advantage of using convolutional layers 504 is that spatially local correlation of the input data can exploited by enforcing a local connectivity pattern between nodes of adjacent layers, in particular by each node being connected to only a small region of the nodes of the preceding layer.

In embodiment shown in FIG. 5, the input layer 502 comprises 36 nodes 512, arranged as a two-dimensional 6×6 matrix. The convolutional layer 504 comprises 72 nodes 514, arranged as two two-dimensional 6×6 matrices, each of the two matrices being the result of a convolution of the values of the input layer with a kernel. Equivalently, the nodes 514 of the convolutional layer 504 can be interpreted as arranges as a three-dimensional 6×6×2 matrix, wherein the last dimension is the depth dimension.

A pooling layer 506 can be characterized by the structure and the weights of the incoming edges and the activation function of its nodes 516 forming a pooling operation based on a non-linear pooling function f. For example, in the two dimensional case the values $x^{(n)}$ of the nodes 516 of the pooling layer 506 can be calculated based on the values $x^{(n-1)}$ of the nodes 514 of the preceding layer 504 as $$x^{(n)}[i,j] = f(x^{(n-1)}[id_1, jd_2], \ldots, x^{(n-1)}[id_1+d_1-1, jd_2+d_2-1])$$

In other words, by using a pooling layer 506, the number of nodes 514, 516 can be reduced, by replacing a number d1·d2 of neighboring nodes 514 in the preceding layer 504 with a single node 516 being calculated as a function of the values of said number of neighboring nodes in the pooling layer. In particular, the pooling function f can be the max-function, the average or the L2-Norm. In particular, for a pooling layer 506 the weights of the incoming edges are fixed and are not modified by training.

The advantage of using a pooling layer 506 is that the number of nodes 514, 516 and the number of parameters is reduced. This leads to the amount of computation in the network being reduced and to a control of overfitting.

In the embodiment shown in FIG. 5, the pooling layer 506 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 508 can be characterized by the fact that a majority, in particular, all edges between nodes 516 of the previous layer 506 and the nodes 518 of the fully-connected layer 508 are present, and wherein the weight of each of the edges can be adjusted individually.

In this embodiment, the nodes 516 of the preceding layer 506 of the fully-connected layer 508 are displayed both as two-dimensional matrices, and additionally as non-related nodes (indicated as a line of nodes, wherein the number of nodes was reduced for a better presentability). In this embodiment, the number of nodes 518 in the fully connected layer 508 is equal to the number of nodes 516 in the preceding layer 506. Alternatively, the number of nodes 516, 518 can differ.

Furthermore, in this embodiment, the values of the nodes 520 of the output layer 510 are determined by applying the Softmax function onto the values of the nodes 518 of the preceding layer 508. By applying the Softmax function, the sum the values of all nodes 520 of the output layer 510 is 1, and all values of all nodes 520 of the output layer are real numbers between 0 and 1.

A convolutional neural network 500 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 500 can be trained based on the backpropagation algorithm. For preventing overfitting, methods of regularization can be used, e.g. dropout of nodes 512-520, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1. Certain steps or functions of the methods and workflows described herein, including one or more of the steps or functions of FIG. 1, may be performed by a server or by another processor in a network-based cloud-computing system. Certain steps or functions of the methods and workflows described herein, including one or more of the steps of FIG. 1, may be performed by a client computer in a network-based cloud computing system. The steps or functions of the methods and workflows described herein, including one or more of the steps of FIG. 1, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 6:
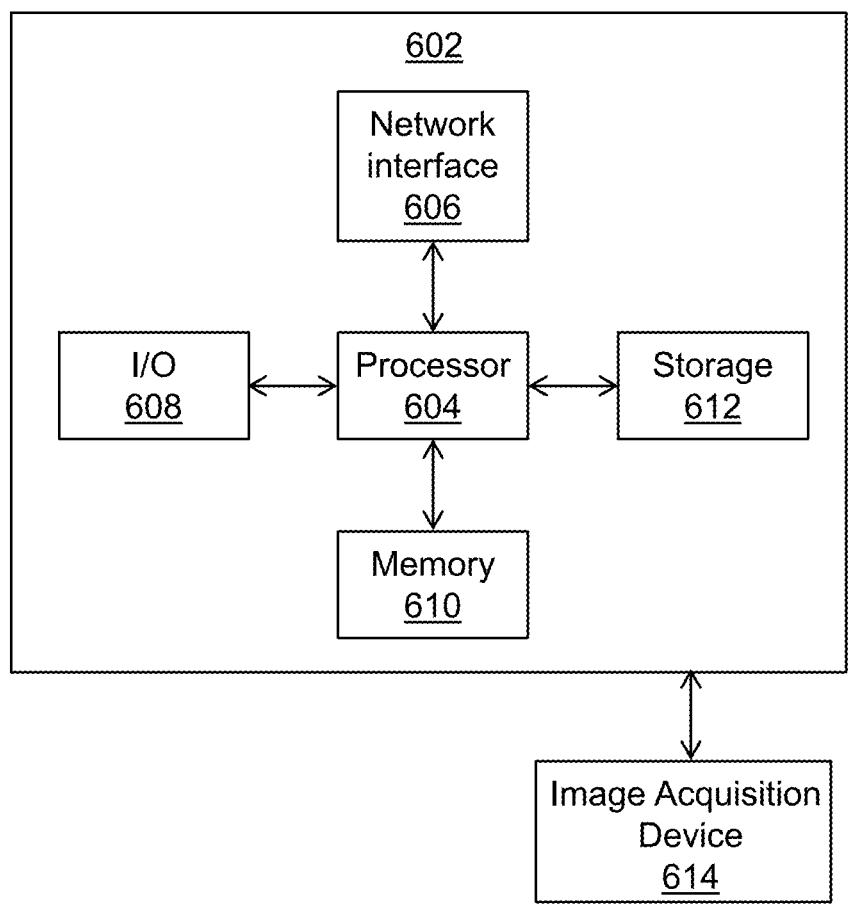
FIG. 6 shows a high-level block diagram of a computer that may be used to implement one or more embodiments.

A high-level block diagram of an example computer 602 that may be used to implement systems, apparatus, and methods described herein is depicted in FIG. 6. Computer 602 includes a processor 604 operatively coupled to a data storage device 612 and a memory 610. Processor 604 controls the overall operation of computer 602 by executing computer program instructions that define such operations. The computer program instructions may be stored in data storage device 612, or other computer readable medium, and loaded into memory 610 when execution of the computer program instructions is desired. Thus, the method and workflow steps or functions of FIG. 1 can be defined by the computer program instructions stored in memory 610 and/or data storage device 612 and controlled by processor 604 executing the computer program instructions. For example, the computer program instructions can be implemented as computer executable code programmed by one skilled in the art to perform the method and workflow steps or functions of FIG. 1. Accordingly, by executing the computer program instructions, the processor 604 executes the method and workflow steps or functions of FIG. 1. Computer 602 may also include one or more network interfaces 606 for communicating with other devices via a network. Computer 602 may also include one or more input/output devices 608 that enable user interaction with computer 602 (e.g., display, keyboard, mouse, speakers, buttons, etc.).

Processor 604 may include both general and special purpose microprocessors, and may be the sole processor or one of multiple processors of computer 602. Processor 604 may include one or more central processing units (CPUs), for example. Processor 604, data storage device 612, and/or memory 610 may include, be supplemented by, or incorporated in, one or more application-specific integrated circuits (ASICs) and/or one or more field programmable gate arrays (FPGAs).

Data storage device 612 and memory 610 each include a tangible non-transitory computer readable storage medium. Data storage device 612, and memory 610, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 608 may include peripherals, such as a printer, scanner, display screen, etc. For example, input/output devices 608 may include a display device such as a cathode ray tube (CRT) or liquid crystal display (LCD) monitor for displaying information to the user, a keyboard, and a pointing device such as a mouse or a trackball by which the user can provide input to computer 602.

An image acquisition device 614 can be connected to the computer 602 to input image data (e.g., medical images) to the computer 602. It is possible to implement the image acquisition device 614 and the computer 602 as one device. It is also possible that the image acquisition device 614 and the computer 602 communicate wirelessly through a network. In a possible embodiment, the computer 602 can be located remotely with respect to the image acquisition device 614.

Any or all of the systems and apparatus discussed herein may be implemented using one or more computers such as computer 602.

One skilled in the art will recognize that an implementation of an actual computer or computer system may have other structures and may contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer implemented method comprising:
receiving a set of input medical images acquired at a plurality of locations on a patient;
sorting the set of input medical images based on the locations;
for each respective location of the plurality of locations:
determining, based on the sorted set of input medical images, an image quality score for each input medical image of the set of input medical images acquired at the respective location, and
selecting one of the input medical images acquired at the respective location based on the image quality scores;
processing the selected input medical images to correct for errors;
segmenting one or more regions of interest from the processed selected input medical images;
calculating one or more hemodynamic measures from the processed selected input medical images based on the segmented one or more regions of interest; and
outputting the calculated one or more hemodynamic measures.

2. The computer implemented method of claim 1, wherein processing the selected input medical images to correct for errors comprises:
processing the selected input medical images to correct for background phase errors.

3. The computer implemented method of claim 1, wherein processing the selected input medical images to correct for errors comprises:
processing the selected input medical images to correct for phase aliasing artifacts.

4. The computer implemented method of claim 1, further comprising identifying one or more anatomical landmarks depicted in the set of input medical images, wherein segmenting one or more regions of interest from the processed selected input medical images comprises:
segmenting the one or more regions of interest from the processed selected input medical images based on the identified one or more anatomical landmarks.

5. The computer implemented method of claim 1, further comprising identifying one or more anatomical landmarks depicted in the set of input medical images, wherein calculating one or more hemodynamic measures from the processed selected input medical images based on the segmented one or more regions of interest comprises:
calculating the one or more hemodynamic measures from the processed selected input medical images based on the identified one or more anatomical landmarks.

6. The computer implemented method of claim 1, wherein the determining, the processing, and the segmenting are performed using a respective machine learning based model.

7. The computer implemented method of claim 1, wherein the determining, the processing, and the segmenting are performed using a single machine learning based model trained with multi-task learning.

8. The computer implemented method of claim 1, wherein the one or more hemodynamic measures comprise one or more of stroke volume, peak velocity inverse flow volume, and regurgitant fraction.

9. The computer implemented method of claim 1, wherein the set of input medical images comprises PC-MRI (phase contrast magnetic resonance imaging) images.

10. An apparatus comprising:
means for receiving a set of input medical images acquired at a plurality of locations on a patient;
means for sorting the set of input medical images based on the locations;
for each respective location of the plurality of locations:
means for determining, based on the sorted set of input medical images, an image quality score for each input medical image of the set of input medical images acquired at the respective location, and
means for selecting one of the input medical images acquired at the respective location based on the image quality scores;
means for processing the selected input medical images to correct for errors;
means for segmenting one or more regions of interest from the processed selected input medical images;
means for calculating one or more hemodynamic measures from the processed selected input medical images based on the segmented one or more regions of interest; and
means for outputting the calculated one or more hemodynamic measures.

11. The apparatus of claim 10, wherein the means for processing the selected input medical images to correct for errors comprises:

means for processing the selected input medical images to correct for background phase errors.

12. The apparatus of claim 10, wherein the means for processing the selected input medical images to correct for errors comprises:
means for processing the selected input medical images to correct for phase aliasing artifacts.

13. The apparatus of claim 10, further comprising means for identifying one or more anatomical landmarks depicted in the set of input medical images, wherein the means for segmenting one or more regions of interest from the processed selected input medical images comprises:
means for segmenting the one or more regions of interest from the processed selected input medical images based on the identified one or more anatomical landmarks.

14. The apparatus of claim 10, further comprising means for identifying one or more anatomical landmarks depicted in the set of input medical images, wherein the means for calculating one or more hemodynamic measures from the processed selected input medical images based on the segmented one or more regions of interest comprises:
means for calculating the one or more hemodynamic measures from the processed selected input medical images based on the identified one or more anatomical landmarks.

15. A non-transitory computer readable medium storing computer program instructions, the computer program instructions when executed by a processor cause the processor to perform operations comprising:
receiving a set of input medical images acquired at a plurality of locations on a patient;
sorting the set of input medical images based on the locations;
for each respective location of the plurality of locations:
determining, based on the sorted set of input medical images, an image quality score for each input medical image of the set of input medical images acquired at the respective location, and
selecting one of the input medical images acquired at the respective location based on the image quality scores;
processing the selected input medical images to correct for errors;
segmenting one or more regions of interest from the processed selected input medical images;
calculating one or more hemodynamic measures from the processed selected input medical images based on the segmented one or more regions of interest; and
outputting the calculated one or more hemodynamic measures.

16. The non-transitory computer readable medium of claim 15, the operations further comprising identifying one or more anatomical landmarks depicted in the set of input medical images, wherein segmenting one or more regions of interest from the processed selected input medical images comprises:
segmenting the one or more regions of interest from the processed selected input medical images based on the identified one or more anatomical landmarks.

17. The non-transitory computer readable medium of claim 15, wherein the determining, the processing, and the segmenting are performed using a respective machine learning based model.

18. The non-transitory computer readable medium of claim 15, wherein the determining, the processing, and the segmenting are performed using a single machine learning based model trained with multi-task learning.

19. The non-transitory computer readable medium of claim 15, wherein the one or more hemodynamic measures comprise one or more of stroke volume, peak velocity inverse flow volume, and regurgitant fraction.

20. The non-transitory computer readable medium of claim 15, wherein the set of input medical images comprises PC-MRI (phase contrast magnetic resonance imaging) images.

* * * * *